US006955647B2

United States Patent
Rice

(12) United States Patent
(10) Patent No.: US 6,955,647 B2
(45) Date of Patent: Oct. 18, 2005

(54) SYSTEM AND METHOD FOR REPETITIVE INTERVAL CLINICAL EVALUATIONS

(76) Inventor: William H. Rice, 78 Pascal La., Austin, TX (US) 78746

( * ) Notice: Subject to any disclaimer, the term of this patent is extended or adjusted under 35 U.S.C. 154(b) by 0 days.

(21) Appl. No.: 10/313,820

(22) Filed: Dec. 6, 2002

(65) Prior Publication Data
US 2003/0233031 A1 Dec. 18, 2003

Related U.S. Application Data

(63) Continuation-in-part of application No. 10/174,498, filed on Jun. 17, 2002.
(51) Int. Cl.[7] .................................................. A61B 5/00
(52) U.S. Cl. ....................................... 600/300; 128/920
(58) Field of Search ................................. 600/300–301; 128/903, 904, 920–921, 925; 340/573.1; 705/2–4; 709/200; 706/924

(56) References Cited

U.S. PATENT DOCUMENTS 5,724,025 A * 3/1998 Tavori ...................... 340/573.1
6,080,106 A * 6/2000 Lloyd et al. ................ 600/300
6,221,009 B1 * 4/2001 Doi et al. ................... 600/300

* cited by examiner

Primary Examiner—Max F. Hindenburg
Assistant Examiner—Michael Astorino

(57) ABSTRACT

A healthcare tool allows a patient to record daily parameters associated with the patient's clinical status, for example, body weight for congestive heart failure patients. A graph may be created showing the parameters on a control chart. The parameters are statistically analyzed against a control range, and when a parameter moves out of the control range, the system automatically creates a pop-up window alerting the patient that the parameter is outside the control range, and that the patient should consider informing a healthcare professional.

32 Claims, 11 Drawing Sheets

FIG. 13A

| | | | | | | | | | | | | |
|---|---|---|---|---|---|---|---|---|---|---|---|---|
| 180 | FAIL RULE 2 (7 DAY LAG)? | | #NA | #NA | #NA | #NA | #NA | #NA | #NA | #NA | #NA | #NA |
| 178 | FAIL RULE 1? | | P | P | P | P | Fail | P | P | P | P | Fail | P |
| 176 | CRITICAL DIFFERENCE FOR RULE 2 | 3.04 | 3.04 | 3.04 | 3.04 | 3.04 | 3.04 | 3.04 | 3.04 | 3.04 | 3.04 | 3.04 |
| 174 | MAX VARIATION FROM MOVING AVERAGE | 3.04 | 3.04 | 3.04 | 3.04 | 3.04 | 3.04 | 3.04 | 3.04 | 3.04 | 3.04 | 3.04 |
| 172 | WEIGHT-MA | #NA | #NA | #NA | #NA | #NA | #NA | #NA | #NA | #NA | #NA | #NA |
| 170 | RULE 1 LIMIT DIFFERENCE IN 2 DAYS (ALWAYS BETWEEN 3-5 BLS) | 4.0 | 4.0 | 4.0 | 4.0 | 4.0 | 4.0 | 4.0 | 4.0 | 4.0 | 4.0 | 4.0 |
| 168 | RULE 1 MINUMUM | 4.0 | 4.0 | 4.0 | 4.0 | 4.0 | 4.0 | 4.0 | 4.0 | 4.0 | 4.0 | 4.0 |
| 166 | CRITICAL DIFFERENCE | 4.03 | 4.03 | 4.03 | 4.03 | 4.03 | 4.03 | 4.03 | 4.03 | 4.03 | 4.03 | 4.03 |
| 164 | SIGMA | 0.99 | 0.99 | 0.99 | 0.99 | 0.99 | 0.99 | 0.99 | 0.99 | 0.99 | 0.99 | 0.99 |
| 162 | REVIS MRBAR | | | | | | | | | | | |
| 160 | REVIS MR | | 4 | 1 | 2 | 1 | 10 | 4 | 13 | 3 | 4 | 9 | 1 |
| 158 | UCLmr | | 38.10 | 38.10 | 38.10 | 38.10 | 38.10 | 38.10 | 38.10 | 38.10 | 38.10 | 38.10 |
| 156 | MRBAR | | 1.12 | 2.12 | 3.12 | 4.12 | 5.12 | 6.12 | 7.12 | 8.12 | 9.12 | 10.12 | 11.12 |
| 154 | MR | | 4 | 1 | 2 | 1 | 10 | 4 | 13 | 3 | 4 | 9 | 1 |
| 152 | DAILY DIFFERENCE | | 4 | -1 | 2 | -1 | 10 | 4 | -13 | 3 | -4 | 9 | 1 |
| 150 | 20-DAY MOVING AVERAGE WITH 7 DAY LAG | | | | | | | | | | | |
| 148 | 20-DAY MOVING AVERAGE | | | | | | | | | | | |
| 146 | PRINCE WEIGHTS | 156 | 160 | 161 | 163 | 162 | 172 | 176 | 163 | 166 | 162 | 171 | 172 |
| 144 | OFFICE | MINOR | MINOR | MINOR | MINOR | MINOR | MINOR | MINOR | GREER | GREER | MINOR | GREER | GREER |
| 142 | DATE | 11/29/99 | 01/10/00 | 03/23/00 | 06/23/00 | 08/09/00 | 12/14/00 | 03/27/01 | 06/13/01 | 08/03/01 | 09/10/01 | 12/06/01 | 03/08/02 |

TO FIG. 13B

FROM FIG. 13A

| 142 | 144 | 146 | 148 | 150 | 152 | 154 | 156 | 158 | 160 | 162 | 164 | 166 | 168 | 170 | 172 | 174 | 176 | 178 | 180 |
|---|---|---|---|---|---|---|---|---|---|---|---|---|---|---|---|---|---|---|---|
| 03/26/02 | MINOR | 172.5 | | | 0.5 | 0.5 | | 12.12 | 38.10 | 0.5 | 0.99 | 4.03 | 4.0 | 4.0 | #NA | 3.04 | 3.04 | P | #NA |
| 04/23/02 | MINOR | 166 | | | -6.5 | 6.5 | | 13.12 | 38.10 | 6.5 | 0.99 | 4.03 | 4.0 | 4.0 | #NA | 3.04 | 3.04 | P | #NA |
| 05/17/02 | GREER | 167 | | | 1 | 1 | | 14.12 | 38.10 | 1 | 0.99 | 4.03 | 4.0 | 4.0 | #NA | 3.04 | 3.04 | P | #NA |
| 08/29/02 | GREER | 162 | | | -5 | 5 | | 15.12 | 38.10 | 5 | 0.99 | 4.03 | 4.0 | 4.0 | #NA | 3.04 | 3.04 | P | #NA |
| 09/26/02 | HOME | 164 | | | 2 | 2 | | 16.12 | 38.10 | 2 | 0.99 | 4.03 | 4.0 | 4.0 | #NA | 3.04 | 3.04 | P | #NA |
| 09/27/02 | HOME | 165 | | | 1 | 1 | | 17.12 | 38.10 | 1 | 0.99 | 4.03 | 4.0 | 4.0 | #NA | 3.04 | 3.04 | P | #NA |
| 09/28/02 | HOME | 165 | | | 0 | 0 | | 18.12 | 38.10 | 0 | 0.99 | 4.03 | 4.0 | 4.0 | #NA | 3.04 | 3.04 | P | #NA |
| 09/30/02 | HOME | 162 | | | -3 | 0 | 3 | 19.12 | 38.10 | 3 | 0.99 | 4.03 | 4.0 | 4.0 | #NA | 3.04 | 3.04 | P | #NA |
| 10/01/02 | HOME | | 165.375 | | -162 | 162 | 11.65 | 38.10 | 12 | 4.13 | 3.66 | #### | 14.9 | 5.0 | #NA | 11.26 | 11.26 | P | #NA |
| 10/02/02 | | | 165.868 | | 0 | 0 | 11.45 | 37.44 | 0 | 3.93 | 3.49 | #### | 14.2 | 5.0 | -165.9 | 10.72 | 10.72 | P | #NA |
| 10/03/02 | | | 166.194 | | 0 | 0 | 11.40 | 37.28 | 0 | 3.88 | 3.44 | #### | 14.0 | 5.0 | -166.2 | 10.58 | 10.58 | P | #NA |
| 10/04/02 | | | 166.500 | | 0 | 0 | 11.30 | 36.95 | 0 | 3.78 | 3.35 | #### | 13.7 | 5.0 | -166.5 | 10.31 | 10.31 | P | #NA |
| 10/05/02 | | | 166.719 | | 0 | 0 | 11.25 | 36.79 | 0 | 3.73 | 3.31 | #### | 13.5 | 5.0 | -166.7 | 10.17 | 10.17 | P | #NA |
| 10/06/02 | | | 167.033 | | 0 | 0 | 10.75 | 35.15 | 0 | 3.23 | 2.87 | #### | 11.7 | 5.0 | -167.0 | 8.81 | 8.81 | P | #NA |
| 10/07/02 | | | 166.679 | | 0 | 0 | 10.55 | 34.50 | 0 | 3.03 | 2.69 | #### | 10.8 | 5.0 | -166.7 | 8.26 | 8.26 | P | #NA |
| 10/08/02 | | | 165.962 | 165.4 | 0 | 0 | 9.90 | 32.37 | 0 | 2.38 | 2.11 | 8.60 | 8.6 | 5.0 | -166.0 | 6.49 | 6.49 | P | P |
| 10/09/02 | | | 166.208 | 165.9 | 0 | 0 | 9.75 | 31.88 | 0 | 2.23 | 1.98 | 8.06 | 8.1 | 5.0 | -166.2 | 6.08 | 6.08 | P | P |
| 10/10/02 | | | 166.227 | 166.2 | 0 | 0 | 9.55 | 31.23 | 0 | 2.03 | 1.80 | 7.34 | 7.3 | 5.0 | -166.2 | 5.54 | 5.54 | P | P |
| 10/11/02 | | | 166.650 | 166.5 | 0 | 0 | 9.10 | 29.76 | 0 | 1.58 | 1.40 | 5.71 | 5.7 | 5.0 | -166.7 | 4.31 | 4.31 | P | P |
| 10/12/02 | | | 166.167 | 166.7 | 0 | 0 | 9.05 | 29.59 | 0 | 1.53 | 1.36 | 5.53 | 5.5 | 5.0 | -166.2 | 4.18 | 4.18 | P | P |
| 10/13/02 | | | 165.438 | 165.9 | 0 | 0 | 9.025 | 29.51 | 0 | 1.51 | 1.34 | 5.44 | 5.4 | 5.0 | -165.4 | 4.11 | 4.11 | P | P |
| 10/14/02 | | | 164.429 | 166.2 | 0 | 0 | 8.7 | 28.45 | 0 | 1.18 | 1.05 | 4.27 | 4.3 | 4.3 | -164.4 | 3.22 | 3.22 | P | P |

*FIG. 13B*

SYSTEM AND METHOD FOR REPETITIVE INTERVAL CLINICAL EVALUATIONS

RELATED APPLICATIONS

This application is a continuation-in-part application of U.S. patent application Ser. No. 10/174,498 entitled "System for Repetitive Interval Clinical Evaluations," filed on Jun. 17, 2002 to William H. Rice, M.D., and incorporates the same by reference.

TECHNICAL FIELD OF THE INVENTION

The present invention relates to healthcare systems and more particularly, to a system and method of modeling chronic disease using a non-linear model together with a set of optimization routines to reduce healthcare costs and improve quality at the same time.

BACKGROUND OF THE INVENTION

More than 90 million Americans live with chronic diseases. Care for these Americans accounts for more than 60% of the nation's medical care costs. By definition, a chronic disease progresses over time with a generally predictable set of costly exacerbations, complications and recurrences.

A central precept to the discussions on health care costs is that there is a cost-quality function from which one may derive a linear cost-quality curve. On such a cost quality curve, so the argument goes, any reduction in the planned budgetary growth of health care dollars will result in lower-quality health care. To the contrary, however, the actual cost-quality curve for health care has been shown to be significantly non-linear. FIGS. 1A and 1B depict the perceived and actual cost-quality curves showing the relationship between cost and health care quality. FIG. 1A depicts an expected cost-quality curve 10, while FIG. 1B depicts the actual non-linear cost-quality curve 12.

In the actual health care cost-quality curve 12 of FIG. 1B, increased costs do not always correlate to improved quality. Instead, there has been shown to be a "quality valley" 14, where health care quality actually decreases 16 with increased expenditures for health care. Understanding this potential "quality valley" 14 is essential to the creation of real improvements and cost savings in health care. That is, if "quality valley" 14 could be either carefully managed against for either its elimination or, if it cannot be eliminated, its avoidance, there could be an opportunity simultaneously decrease costs and improve quality.

Research for two common medical diagnoses, congestive heart failure (CHF) and pneumonia, for example, indicates a wide variation in outcomes among providers. By matching severity-adjusted mortality data to hospital-specific charge data, one can observe that higher average charges often associate with a lower quality of care.

These results support the conclusion that significant variation in charges exists among hospitals. These variances may imply that higher costs associate with lower quality (resulting, for example, in higher severity-adjusted mortality rates). This represents unnecessary resource utilization.

Making comparisons among the ten countries having the highest Gross Domestic Product (GDP) per capita further validates this conclusion. Data from the United States Statistical Abstract indicates that the United States spends the largest percentage of its gross domestic product (GDP) on health care, while exhibiting one of the world's lowest life expectancy at birth (LEAB rates). International health expenditure studies are difficult to conduct, however, because of factors such as data quality, variable accounting methods, and significant social-cultural differences. Despite these shortcomings, a highly reasonable conclusion remains that, with the present systems and methods for managing diseases such as CHF and pneumonia, spending more dollars on health care results in a decrease in health care quality received, as measured on a large scale, for example, by LEAB rates.

Although every physician should consider the best interests of his/her patients, the medical system has evolved with a history of incentives, threats (e.g., medical malpractice), and customs that can significantly increase costs, while not improving quality.

Additionally, disease intervention processes and treatments, all too frequently seek to improve patient comfort, longevity, and physical functioning. These processes and treatments employ surrogate endpoints based on logical, but unproven, extensions of an existing, but incomplete, disease process model. A great number of physician actions are based on these surrogate endpoints. These surrogate endpoints, however, often lead to increased costs and examinations without improved results.

A need exists, therefore, for significant efforts to optimize the cost and quality relationship of healthcare. Prior efforts focus on the development of "best practices" protocols, medical error reduction, bulk purchasing and pharmaceutical benefits management, new medicine, minimally invasive surgery, and the redesign of care systems. These efforts seek to more effectively manage demand for health services. While past practices are important, these efforts fail to address any way to reduce costs and improve quality in healthcare. In particular, they already fail to provide for complication identification and proactive symptom treatment of chronic disease exacerbation in the individual patient.

One avenue of attempting to better practice early complication identification and proactive symptom treatment has been through the use of computers. Such attempts to use computers, for example, seek to automate more routine aspects of medical processes and treatments. These computerized schemes, for example, may center on communicating automatically with a patient regarding a previously diagnosed disease. In such processes, automatic therapy adjustment becomes responsive to information received from the patient. Such automated schemes of medical treatment typically involve the use of computers and the Internet to treat patients remotely. The purpose of these conventional schemes of remote treatment by using computers or Internet avoids unnecessary office visits, thereby effecting savings in overall healthcare costs. Thereby, a physician may be virtually "present" at the patient's location and help treat the patient remotely.

Unfortunately, attempts to automate patient-physician communications do not change previous paradigms for certain chronic diseases. With many of these chronic diseases, infrequent physician visits, either in person or through a virtual office, are accepted as normal. Thus, it has not been possible to identify evolving complications, exacerbations or recurrences, within certain classes of chronic disease patients. At the same time, early interventions may mitigate a patient's worsening clinical condition. In fact, in many instances, early interventions may avoid the need for emergency medical services altogether. Also, disease predictive models have not proven effective to predict the worsening of a patient's condition from chronic diseases. Because of these and other reasons, a standardized therapy based upon broad demographic models is difficult or impossible to employ remotely.

A need exists, therefore, for a system and method that allow early detection of chronic disease exacerbations or complications in order to decrease the need for emergency medical services while measurably improving patient outcomes.

Returning to the above discussion regarding the health care cost-quality curve, often chronic diseases, such as CHF, exhibit a non-linear cost-quality relationship. Accordingly, managing a patient's condition preventively, as opposed to remedially, may assist in avoiding a "quality valley." That is, such preventive management could avoid the situation of increased health care expenditures, ironically, resulting in lower returns in patient outcome. If it were possible to achieve early detection of chronic disease exacerbations or complications, well before the greater cost treatments are necessary, then the health care industry could avoid troubling regions of a non-linear cost-quality curve. In a larger sense, therefore, there is a need for an early detection method and system making it possible to greatly reduce overall health care costs while improving patient quality of life.

SUMMARY OF THE INVENTION

The present invention provides a computer-implemented method for the earliest identification of an exacerbation or complication relating to a chronic condition within a patient. A series of regular repetitive measurements are taken on a set of disease-associated parameters. A history of these parameters is compiled and evaluated using various statistical methods and knowledge of the particular disease. Potential worsening conditions are identified proactively. Once identified, secondary prevention techniques may be employed to prevent the exacerbation and, in doing so, reduce the associated health care cost, while improving the patient's quality of life.

Another embodiment provides a health parameter statistical control measurement tool for improving or optimizing chronic disease care. The system may employ a linear or non-linear optimization model using repetitive, internal, clinical evaluations (i.e., repetitive monitoring) as a primary tool for the earliest possible detection of the onset of a worsening clinical condition. This is especially true for patients whose conditions are sensitive to slight changes in their physician and/or emotional conditions, for example. This condition may be associated with a specific chronic disease diagnosis of previously unidentified conditions, the tracking of a critical care pathway, or rehabilitation.

In some embodiments, patients themselves conduct the repetitive, interval, clinical evaluations and provide the results of these evaluations to a statistical or measurement process, such as a computer program using data associated with the patient's condition. The parameters are then compiled and compared to identify statistical trends or clinical conditions. If one or more parameters fall outside a predetermined statistical control range, the process alerts patient to follow-up with appropriate healthcare team practitioners, such as a nurse or physician. Alternately, the present invention may automatically alert a healthcare practitioner of a condition requiring or suggesting a direct contact with the patient.

Advantageously, the system of the present invention allows for early detection of chronic disease care exacerbations or complications. Accordingly, the present invention supports a decrease in the need for health care services, while measurably improving clinical outcomes for the most common diagnoses of chronic disease patients.

Still further, the present invention promotes general cost and treatment optimization of health care provisions on a larger scale, due to the ability to treat patients in a preventive, instead of a remedially, manner. By identifying trends in an individual patient's condition, the present invention guides or directs the use of reduced or preventive healthcare measures. Such measures frequently are more economical and effective than remedial treatments. This results in movement of the individual patient to a more cost-effective position on the health care cost-quality curve. Therefore, collectively, a great number of chronic disease patients moving to these more effective areas on the health care cost-quality curve will normally improve the effectiveness, or return on expenditure, for health care processes and treatments.

In one embodiment of the invention, a process derives a critical difference as a rolling average of twenty measurements as the basis for repetitive, interval, clinical evaluations, but using a seven-measurement lag and three times the moving sigma, based on twenty prior measurements, as specified in detail below. For purposes of the present embodiment and in the case of CHF, the seven-measurement lag may represent, for example, the set of twenty measurements where the most recent measurement occurred seven days ago and the least recent occurred twenty-seven days ago, with daily measurements occurring each of the intervening days. In another embodiment, a different set of measurements might be more appropriate to take than the twenty measurements and seven-day lag used in the CHF case.

BRIEF DESCRIPTION OF THE DRAWINGS

The present invention will be described with particular embodiments thereof, and references will be made to the drawings in which:

FIGS. 13A–B show one view of a computer spreadsheet having embedded formulae which an embodiment of the present invention may use to record, manipulate, and present information to an interface such as those of FIGS. 5 through 12.

DETAILED DESCRIPTION OF THE INVENTION

Figure 1A:
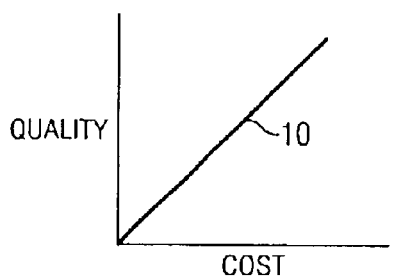
FIGS. 1A and 1B illustrate perceived linear and actual non-linear relationship between health care costs and quality of care.

The present invention provides a method and system for improved identification and evaluation of exacerbations and complications relating to chronic diseases. One embodiment of the present invention relates to a system to optimize chronic disease care. For purposes of the present invention, chronic disease care optimization may be defined as the process of early identification of exacerbations, complications and recurrences. Early identification allows a patient to alert his healthcare provider, receive preventive or early stage remedial treatments, and/or avoid costly and intensive remedial medical interventions and/or hospitalizations. The collected data leads to early identification and the opportunity for alerting the patient or the health care provider of a situation.

One embodiment of the present invention may use a non-linear model, such as a chaotic model. However, various non-linear models may be envisaged. In chaotic models, a sensitive dependence exists on model initial conditions and assumptions. Mathematically, the initial conditions of a system, when varied by an exceedingly small amount, can result in widely variable outcomes without a distinguishable pattern.

In a chaotic or complex system, repetitive measurements improve the ability to model and predict future conditions. Weather prediction provides a classic example of non-linear systems with "chaotic" or "complex" components. The National Oceanographic and Atmospheric Association (NOAA), a component of the U.S. Department of Commerce, gathers data and predicts the weather. Several decades ago, as mainframe computers became available to solve large data set problems, programs to model weather systems began to evolve from improving NOAA's weather predicting ability. Soon, NOAA discovered that if the input data of the program varied by some exceedingly small amount (e.g., if barometric pressure at some location increased by an un-measurable thousandth of an inch), then the model output differed drastically.

Optimizing a non-linear system with a "chaotic" component employs repetitive data sampling where the critical element is the periodicity of the data sampling. The best possible weather predictions, for example, depend on frequent measurements over time. More intensive measurements taken less frequently are not a reliable approach for optimizing weather prediction.

Now, a repetitive data sampling system has direct applications to healthcare. For example, one embodiment of the present invention may be used to identify problems associated with the care of a patient diagnosed with congestive heart failure (CHF). CHF is characterized by a heart muscle that cannot pump blood effectively. Patients with CHF generally have difficulty breathing because excess fluids "behind" a weakened heart accumulate in the lungs. Care for CHF patients includes medicines such as diuretics to improve breathing by removing excess fluids. With the removal of excess fluids, the patient's lungs become "clear," which allows the patient to breathe more normally.

Because water is the primary component of the human body, body weight measurements (on an ongoing basis) are an excellent indicator of the clinical status of a patient with CHF. Current care of most CHF patients includes visits to physicians' offices approximately every 3 to 6 months, depending on the severity of symptoms. By monitoring body weight twice a week, hospitalization rate and corresponding costs can be reduced by approximately 50–90%. Thus, cost has been reduced and quality of life has improved. Repetitive clinical monitoring of body weight, for example, twice a week, in CHF patients should be the "standard of care."

Just as weather prediction may be viewed as a chaotic system, so too may prediction of emergency conditions with chronic diseases be considered a chaotic system problem. It should be noted here, however, that the present invention is not limited to applications in CHF, but may have use in applications to other chronic diseases such as, but not limited to, diabetes, asthma, emphysema, cancer, and other cardiovascular diseases known to those skilled in the art.

Nonetheless, CHF provides an excellent case for applying the teachings of the present invention, since CHF patients represent the largest disease class and the most commonly hospitalized group of individuals over the age of 65 in the United States. Just as two weather conditions may, in almost all salient aspects, appear virtually identical, two CHF patients may appear much the same on one day, but exhibit drastically different conditions in only a very short span of time. In one example, two CHF patients could "look" clinically identical in two discrete observations having the exact same medical histories, lifestyle, and clinical findings and can be seen, diagnosed and treated at the exact same time in the exact same way. However, these discrete observations lack any historical trends. One cannot accurately predict which patient will progress with an uneventful clinical course and which patient will deteriorate and need intensive care without additional data.

This example of two "identical" patients may be considered as analogous to the weather system model in that the two "identical" weather conditions exhibiting two seemingly identical initial conditions (differing barometric pressure by an un-measurable thousandth of an inch). Only repetitive monitoring will cause historical trends to distinguish between patients in many instances.

Interestingly, an individual's body weight provides an easily measured parameter that enables prediction of likely exacerbations and complications in CHF patients. CHF patients have occasional exacerbations that require hospitalization and intensive care. However, a predictable sequence of symptoms and findings precedes the patient's "decomposition." CHF patients often begin a pattern of weight gain. This progression of an easily measured parameter provides a window of opportunity for emergency condition prevention in CHF patients. Mitigation of disease exacerbations consists primarily of alerting the patient, and eventually, the healthcare provider team of the weight gain trend. When the healthcare team knows that a CHF patient is gaining weight, the treatment can be changed. For example, incremental doses of diuretics, changes in diet and other measures can very effectively prevent the acute clinical exacerbation.

Thus, in chronic disease care, more frequent data inputs can result in earliest detection of clinical exacerbations and complications. In this instance, secondary prevention can address an evolving problem before the problem incapacitates the patient and requires intensive, expensive, and, often times, less successful medical intervention.

Figure 2:
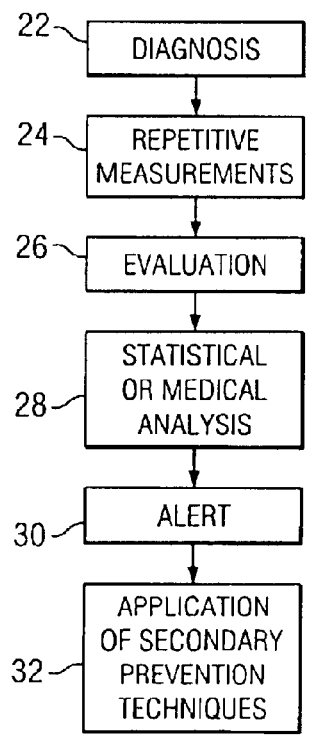
FIG. 2 provides a flowchart depicting one embodiment of the method provided by the present invention.

The present invention, therefore, includes a method and process to support the more frequent collection of relevant chronic disease data, which may avoid the need for such interventions. Referring to FIG. 2 to understand the present inventions, there appears a flow chart depicts a repetitive, interval, clinical evaluation method 20 consistent with the teachings of the present invention. In step 22, a patient may be diagnosed with a chronic disease or condition. This disease or chronic condition may have a specific set of disease-associated parameters that may be measured by the healthcare team in a clinical environment or the patient at home.

These parameters may be either objective measurements, such as the patient's weight, as discussed previously, or subjective measurements, as when dealing with other conditions such as mental disease. The patient or healthcare provider in step 24 measures the parameters. These measurements are then compiled by a computer program as part of the patient's historical record. The instant measurements are evaluated for potential data entry errors or indication of immediate healthcare problems in step 26. In step 28, the overall history of measurements is studied to identify statistical or medical indicators of worsening conditions or potential problems. The patient or healthcare team is then alerted at step 30 to potential future problems. This alert allows secondary prevention techniques to be applied to the patient's condition. This allows the disease condition to be treated in a proactive rather than reactive manner, such as through the application of secondary prevention techniques at step 32. Furthermore, this allows patient quality of life to increase while reducing healthcare costs. Furthermore, this approach, when taken on a macroscopic scale, can significantly decrease healthcare costs of an individual medical practice, a hospital system or geographical region.

Figure 3:
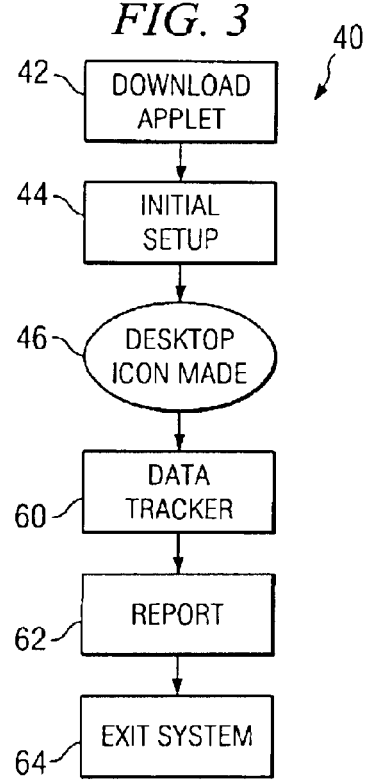
FIG. 3 gives a flow diagram illustrating one embodiment of a process performed by the system of the present invention.

FIG. 3 illustrates the flow of one embodiment of a process 40 that a computer may implement as part of the present invention. In step 42, process 40 starts by downloading a program application, for example, a JAVA applet from a Web server. The JAVA applet may run on a patient's computer using a JAVA-compatible Web browser, such as Netscape Navigator or Microsoft Internet Explorer. It should be noted that if a second patient desires to also use the system, the program application may be written to accommodate additional patients or, alternatively, the second patient may download the JAVA applet another time, in order, for example, to keep the associated patient information separate.

Figure 4:
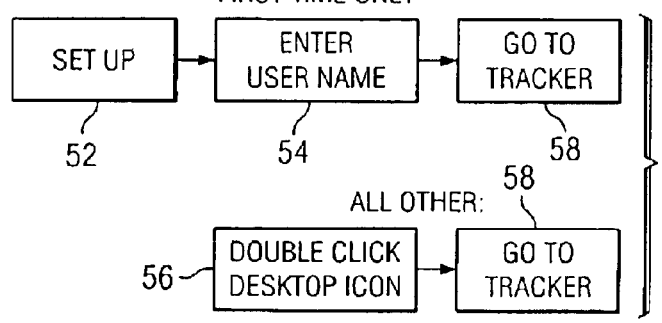
FIG. 4 shows a set-up process which a patient may employ in using an embodiment of the present invention.

In step 44, after the JAVA applet is downloaded, the patient initially sets up the system. In step 46, the process creates a desktop icon. FIG. 4 illustrates an example of the set up process 50 according to an embodiment of the present invention. So, referring to FIG. 4, in step 52, set up occurs, and in step 54, a first time patient inputs an identifying name. The process then continues to the health parameter statistical control measurement tool. A repeat patient, in step 56, simply double clicks on a desktop icon to enter the program, and then the process goes, via step 58, to the health parameter statistical control measurement tool.

Referring back to FIG. 3, process 40 proceeds to the health parameter statistical control measurement tool at data tracker step 60. The health parameter statistical control measurement tool receives inputs or parameters associated with a particular patient's health condition or clinical status. The health parameter statistical control measurement tool will be described in more detail below with respect to FIGS. 5–9.

In step 62, process 40 generates a report, which may include a graph covering a desired time frame selected by the patient. In exit system step 64, the process reaches an endpoint. These steps will be explained in more detail below with respect to FIGS. 10–12.

Figure 5:
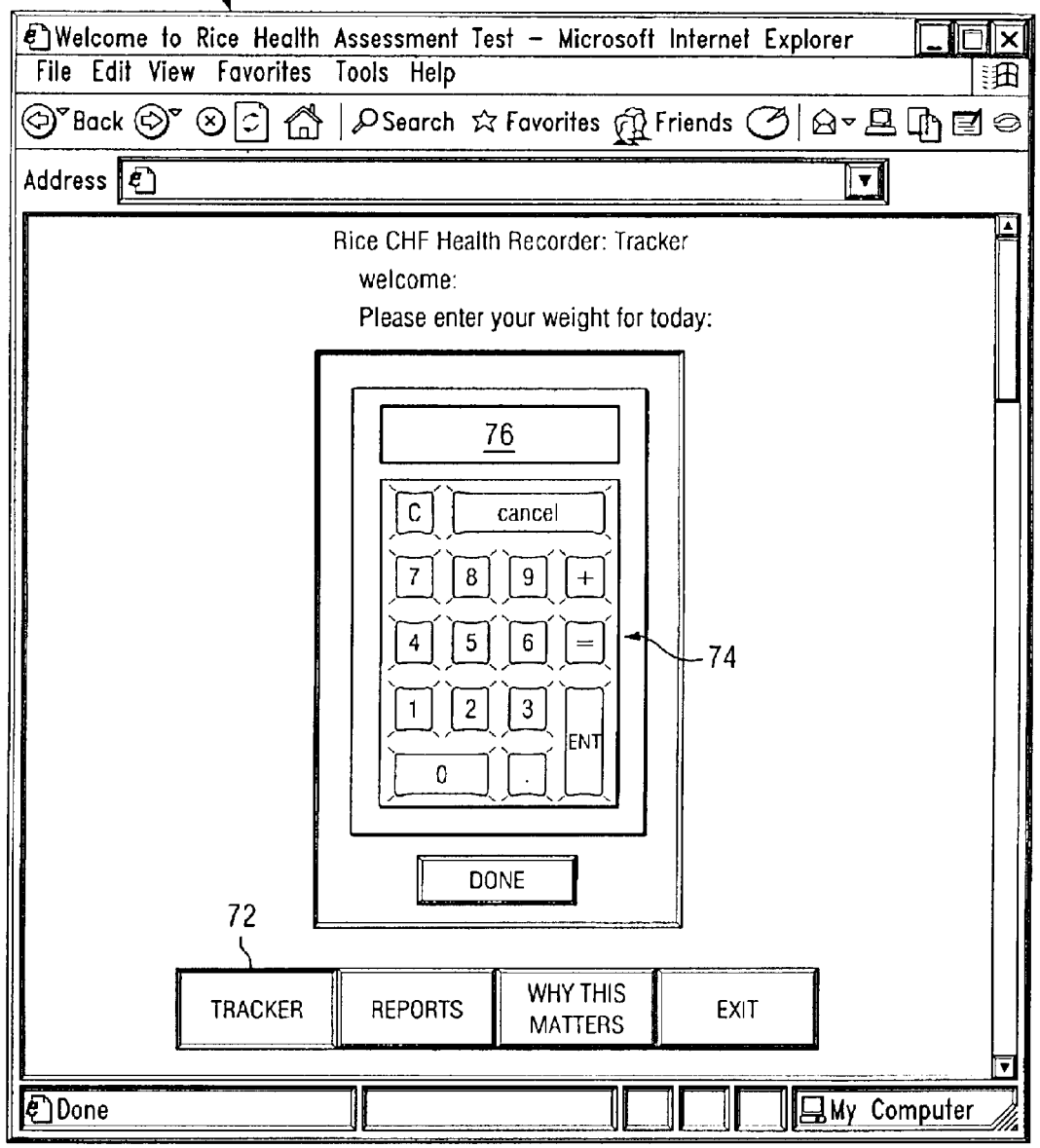
FIGS. 5–8 and 9A–B present exemplary screen shots of the steps performed by the health parameter statistical control measurement tool according to an embodiment of the present invention.

FIGS. 5–9 present exemplary screen shots, such as screen shot 70 of FIG. 5, to illustrate the steps performed by the health parameter statistical control measurement tool of the present invention. After a patient signs into the system, the system goes to health parameter statistical control measurement tool as indicated by the highlighted "TRACKER" button 72 of screen shot 70 of FIG. 5.

The system will be here described in conjunction with an application for a CHF patient, wherein the system tracks the parameter of a CHF patient's body weight as a way to prevent chronic disease condition exacerbations. Because many other chronic diseases have easily measured parameters highly associated with the patient's clinical status, the system of this invention can be broadly applied to the care of these diseases as well. Chronic diseases in the United States that may be tracked include, but are not limited to:

asthma, for which peak flow can be measured; chronic obstructive pulmonary disease (emphysema), for which flow can be measured;

diabetes, for which glucose can be measured;

other cardiovascular diseases such as arrhythmia, infarction, ischemia, arteriosclerosis for which number of nitroglycerin tablets taken daily, number of chest pain episodes, ambulation distance without pain, minutes walking without pain, etc. can be measured;

rehabilitation, such as from hip and knee replacements, for which ambulation paces/activity can be measured; or cancer, post chemotherapy/post radiation of toxicity such as food/liquid intake, etc. can be measured.

Following a prompt from a computer supporting the present invention's process, a CHF patient or healthcare worker may enter the patient's measured body weight or other measured parameters. In the embodiment shown in FIG. 5, the patient clicks on number pad 74, which appears on screen 70 to enter the weight, which appears in display area 76.

Figure 6:
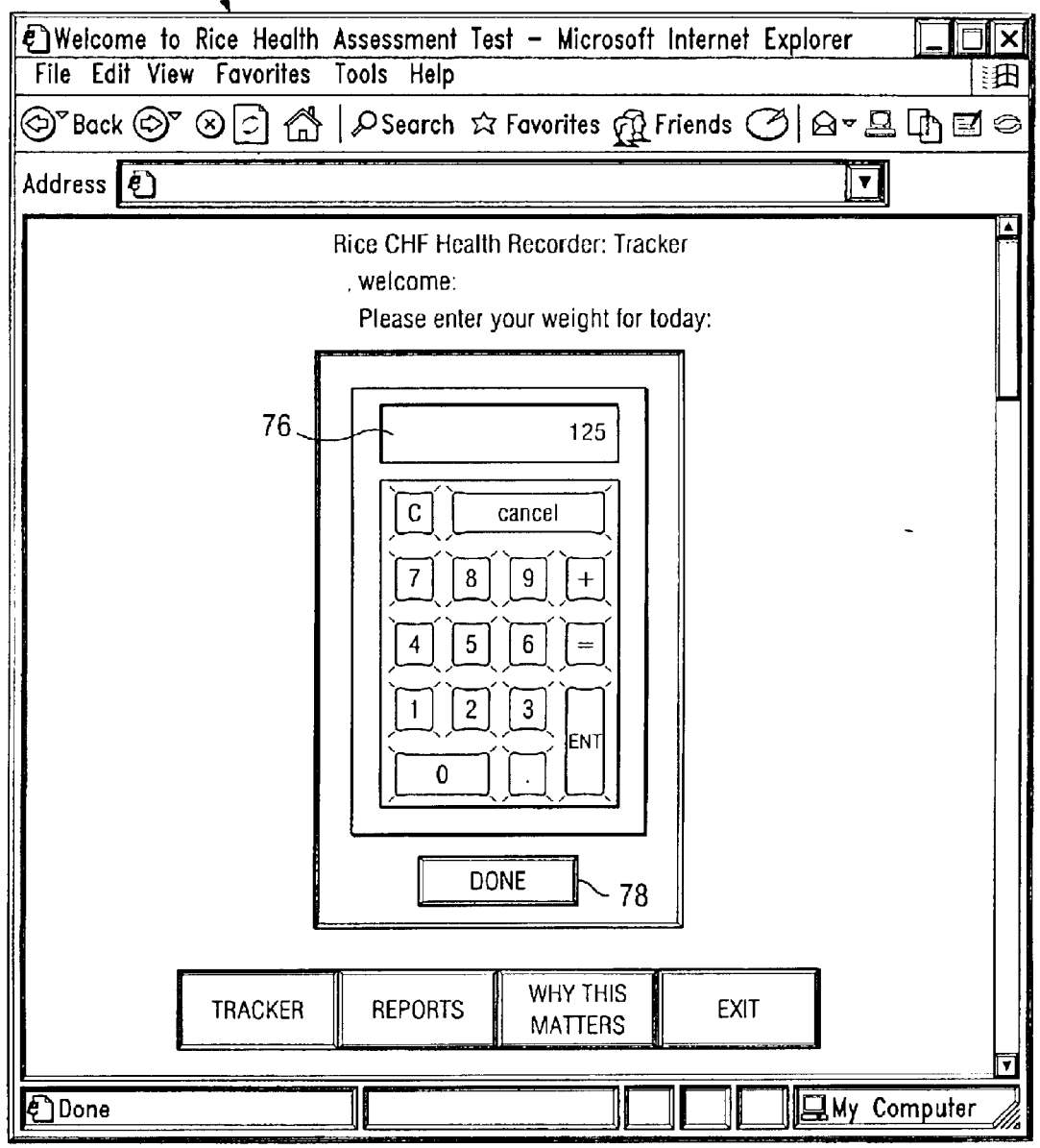

FIG. 6 illustrates an example in which the patient entered a weight of 125 in display area 76. Once the patient enters the weight, the button 78 labeled "Done" may be pressed to continue. It should be noted that in other embodiments, the patient might be asked to confirm the entry. Other methods of data entry, either manual or automated, as known to those skilled in the art, may be used to facilitate the process.

Figure 7:
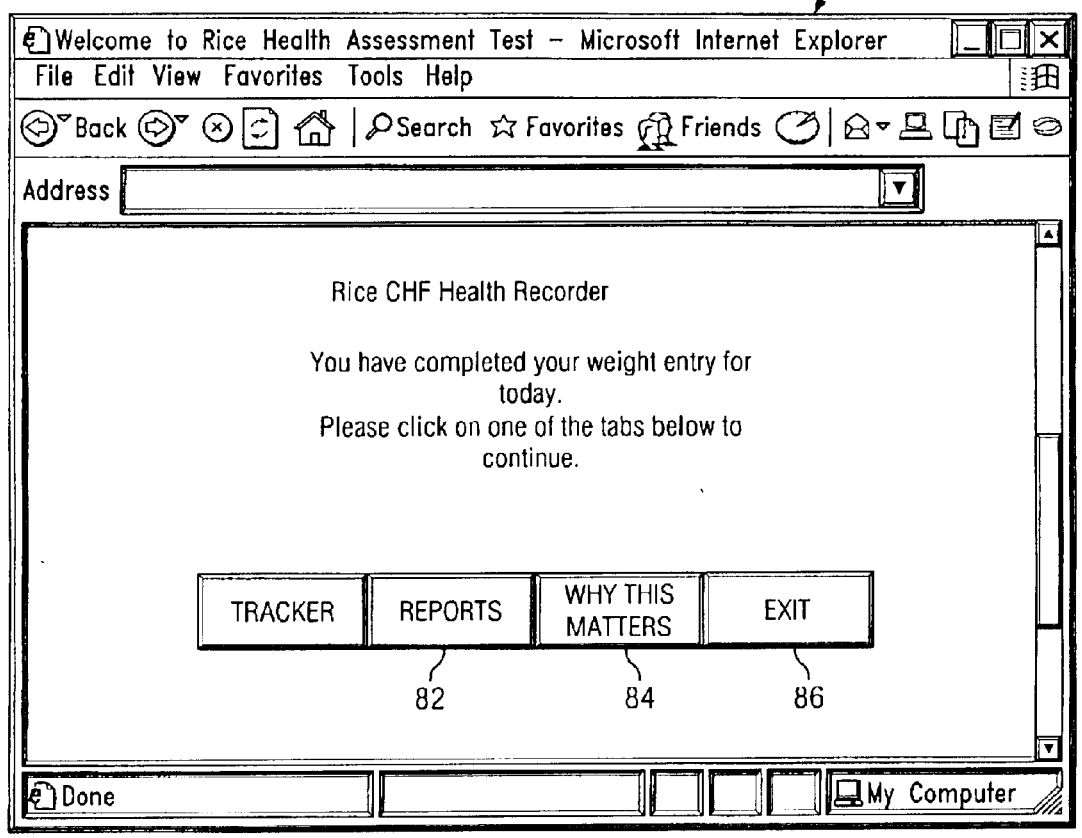

FIG. 7 provides the next exemplary screen shot 80 where the patient may confirm that he has completed the weight entry for the day. Next, the process prompts the patient to click on the appropriate tab to continue. As shown, the patient may have several options. For example, the patient may choose to receive a report by clicking on the "REPORTS" icon 82, information on "WHY THIS MATTERS" by clicking on icon 84, or exit the system by clicking on the "EXIT" icon 86.

Figure 8:
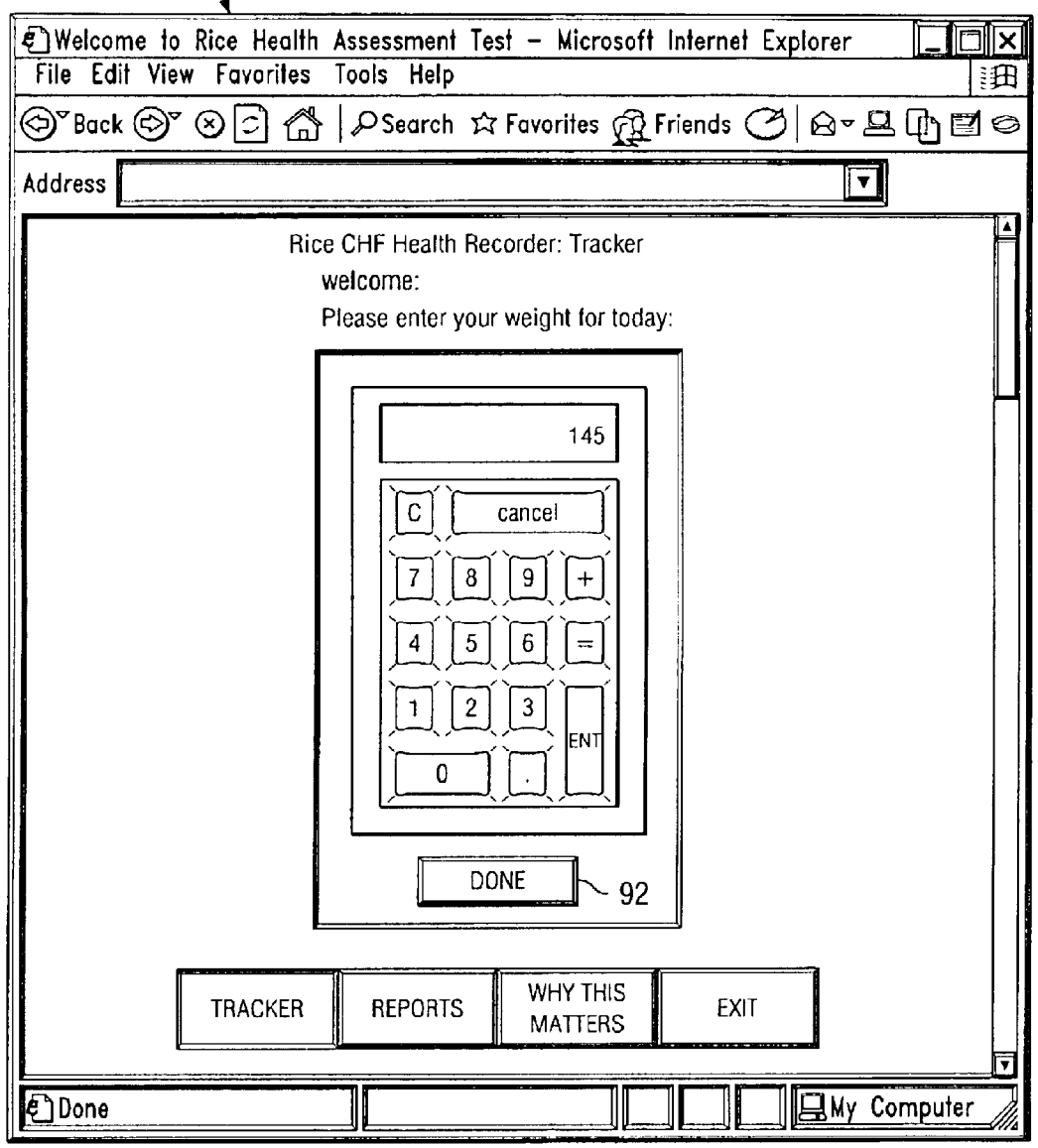

In FIG. 8, screen shot 90 indicates that the patient entered a weight of 145 the next time. Once the patient enters the weight, icon 92 labeled "Done" is clicked to continue. It should be noted that in other embodiments, the patient might be asked to confirm the entry.

Figure 9A:
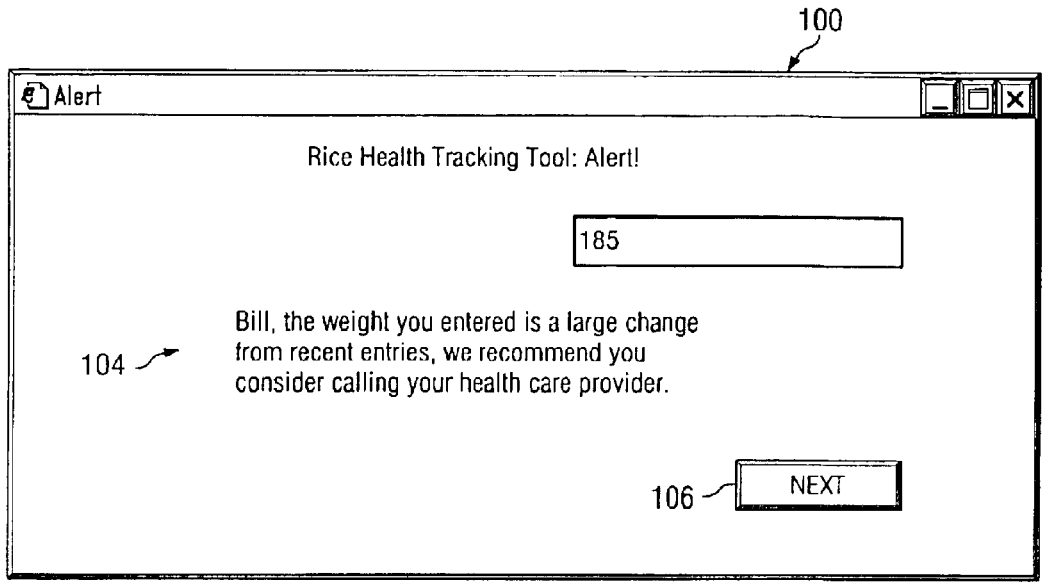
Figure 9B:
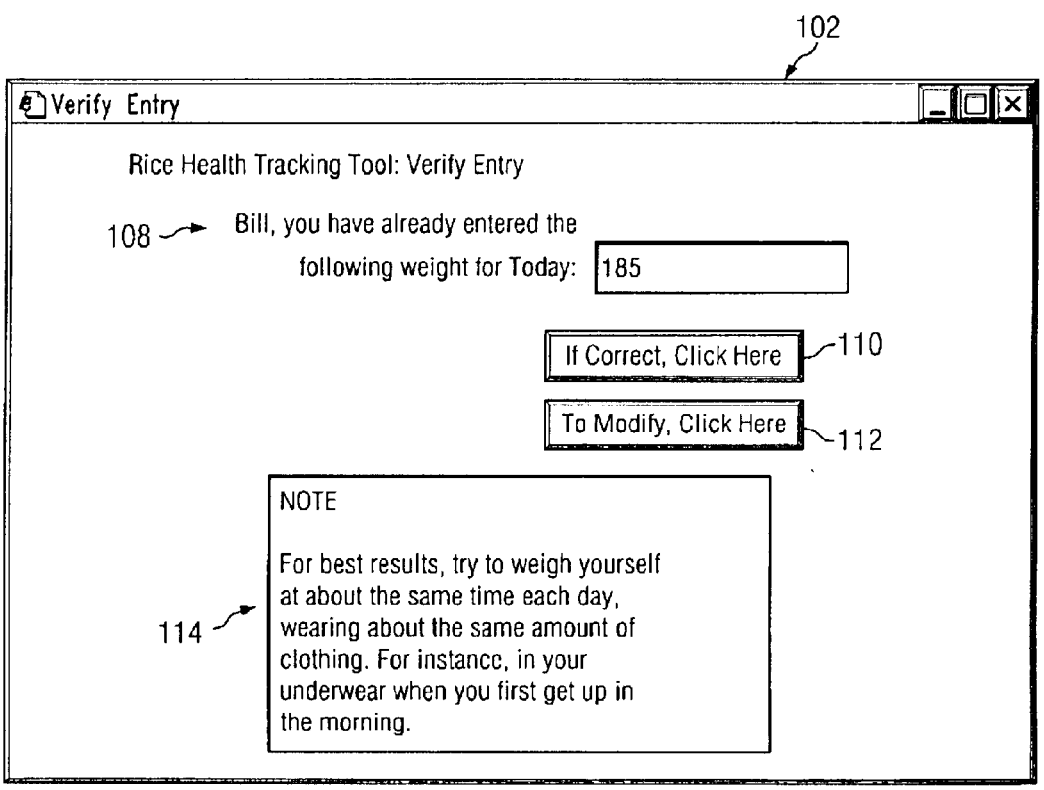

FIGS. 9A and 9B illustrate further exemplary screen shots 100 and 102, respectively. In FIG. 9A, the body weight entered of 185 exceeds a control range for the particular patient, causing the system to give the patient an "Alert" report 104, for example, with the words that "Bill, the weight you entered is a large change from recent entries, we recommend you consider calling your healthcare provider." Next icon 106 allows the patient to progress to screen 102 of FIG. 9B.

Because the weight of 185 is entered after the initial entry of 125 on the same day, FIG. 9B shows a subsequent screen shot with a message 108 stating, for example, that "Bill, you have already entered the following weight for today." Icons 110 and 112 permit, respectively, the patient to confirm that the entry is correct by clicking "If Correct, Click Here" or to modify by clicking "To Modify, Click Here." A message 114 guides the patient with the statement that "For best results, try to weigh yourself at about the same time each day, wearing about the same amount of clothing. For instance, in your underwear when you first get up in the morning." Other steps, as known to those skilled in the art, and messages may be taken to ensure the coherency and integrity of the data collection process.

The present invention performs a statistical analysis on the data collected through the above screens using an averaging program and self-comparison of data. The system may use a control range established by the Deming statistical method, or other methodologies as known to those skilled in the art. In one example, when the weight of the patient exceeds about three percent of the control range, the system produces an Alert to the patient.

Statistical analyses steps for congestive heart failure may include establishing a base line weight associated with an initial stable condition for the patient. The system will then perform an analysis under consistent guidelines to establish weight data for future measurements. Then, the process will have the patient record his weight data and compare the data to baseline. This will permit a determination of a percentage weight change from the base line. In the preferred embodiment, if the percentage weight change represents a weight greater than a set percentage for the patient, the present invention will generate an alert.

These control limits may be based on the individual and the population as a whole. For example, the system may identify a trend of increasing weight for the individual or the fact that the individuals weight has exceeded an accepted value based on the individual's sex/height and age.

Statistical analysis for other disease conditions can be approached in a similar manner. That is, with other diseases a baseline for one or more parameters may be set. Frequent subsequent data may then be collected from the patient relating to or containing measurements of the specific parameters. Statistical changes for parameters then may be established, based in part upon the character of the disease process and the particular details of the patient. The statistical changes that are used to analyze the patient will be dependent upon the disease, the volatility inherent in the data being measured, and other factors as known to those skilled in the art.

Figure 10:
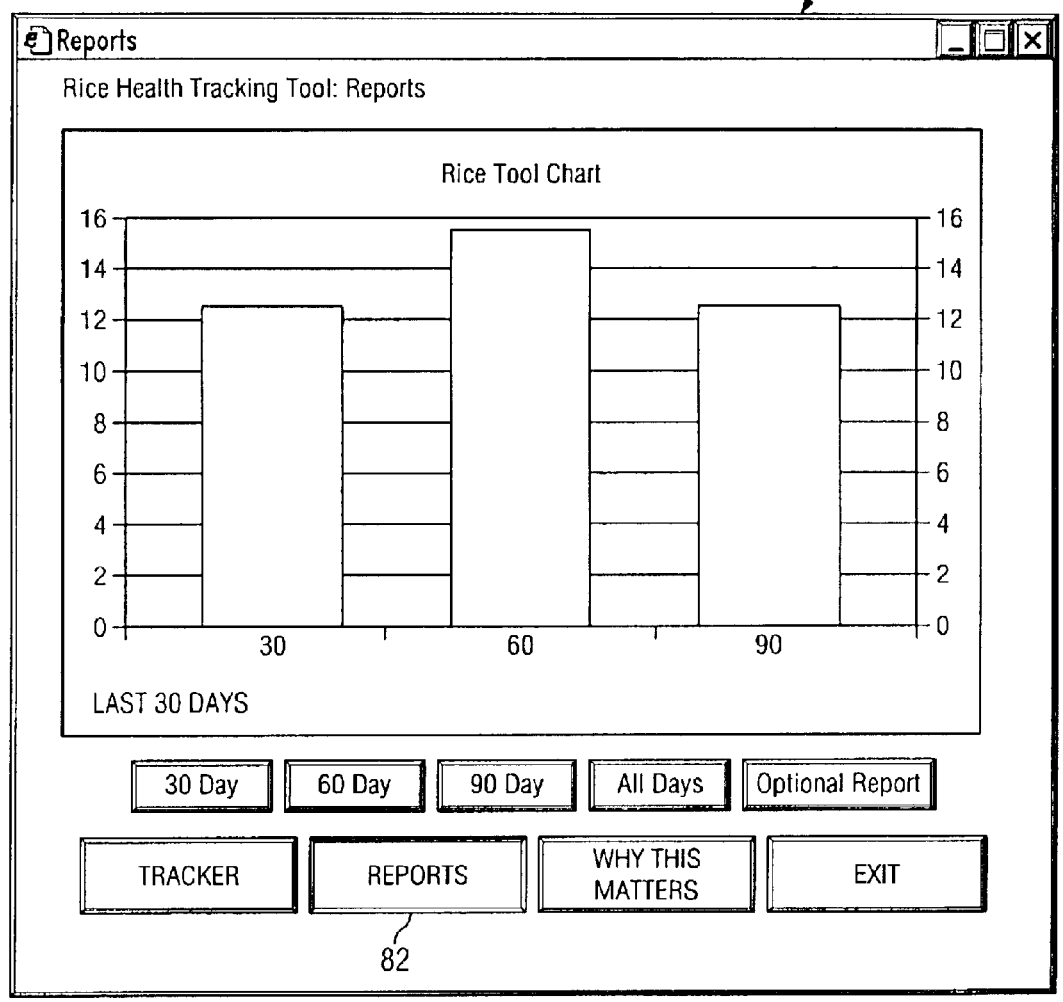
FIG. 10 depicts an exemplary screen shot of a "Report" according to an embodiment of the present invention.

In FIG. 10, exemplary screen shot 120 presents a graphical report that the present invention may provide. As discussed previously, the patient may choose to obtain a report by simply pressing "REPORTS" button 82. The report may track parameter(s) associated with the patient's clinical status. In the example shown, a graph of the measured body weight over a specified period of time is provided. The patient may choose the period of time reported, such as ten days, or thirty days, or another time interval.

Figure 11:
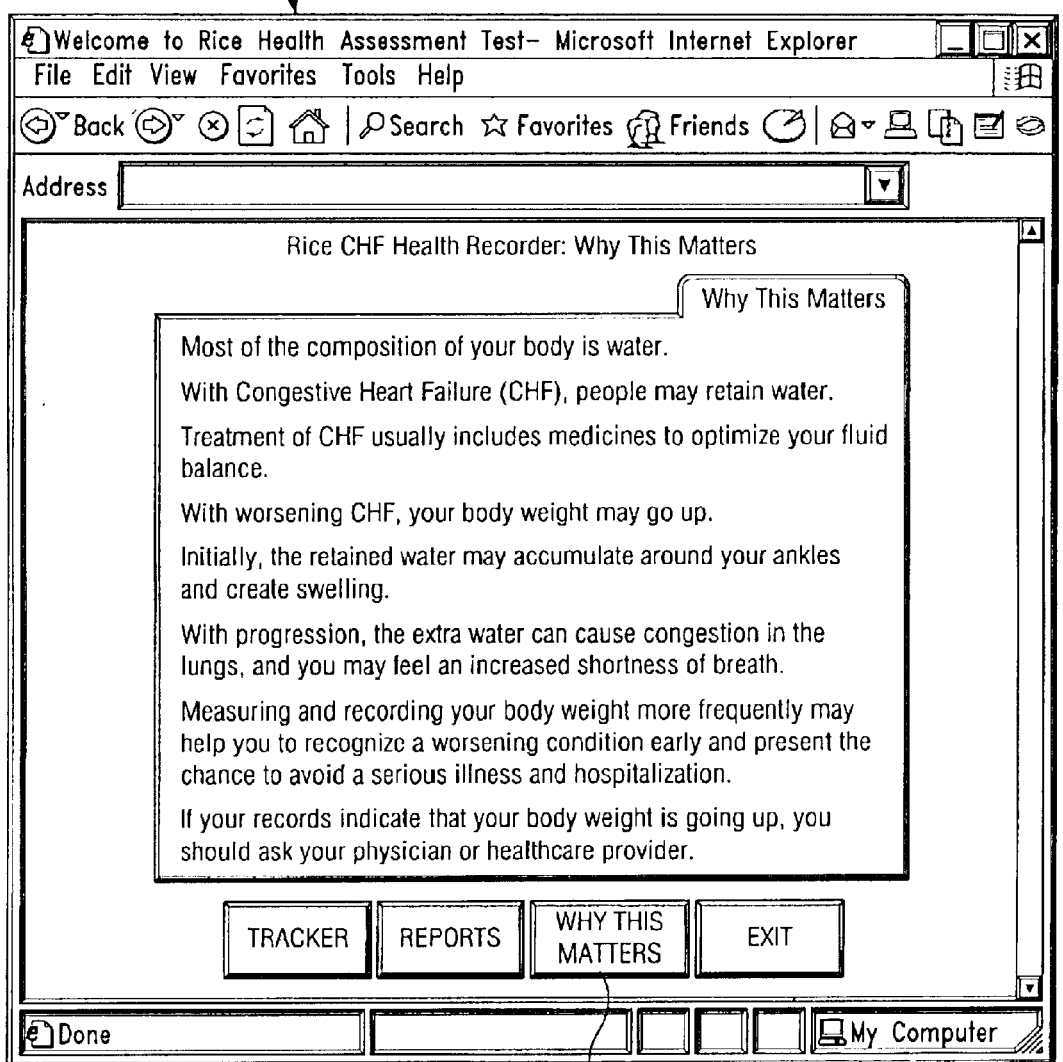
FIG. 11 portrays an exemplary screen shot of an additional alerting step according to an embodiment of the present invention.

In FIG. 11, screen shot 122, explains the importance of tracking those parameter(s) to the patient. The patient may obtain more information on the significance of the tracking of the parameters by simply pressing "WHY THIS MATTERS" button 124. Exemplary screen shot 122 explains the importance of tracking weight in CHF patients and prompts the patient to call a physician or healthcare provider if the records indicate that his body weight is increasing. In another embodiment, the system may send an alert to the patient's healthcare team to initiate the process where the healthcare team then contacts the patient to schedule a physical examination.

Figure 12:
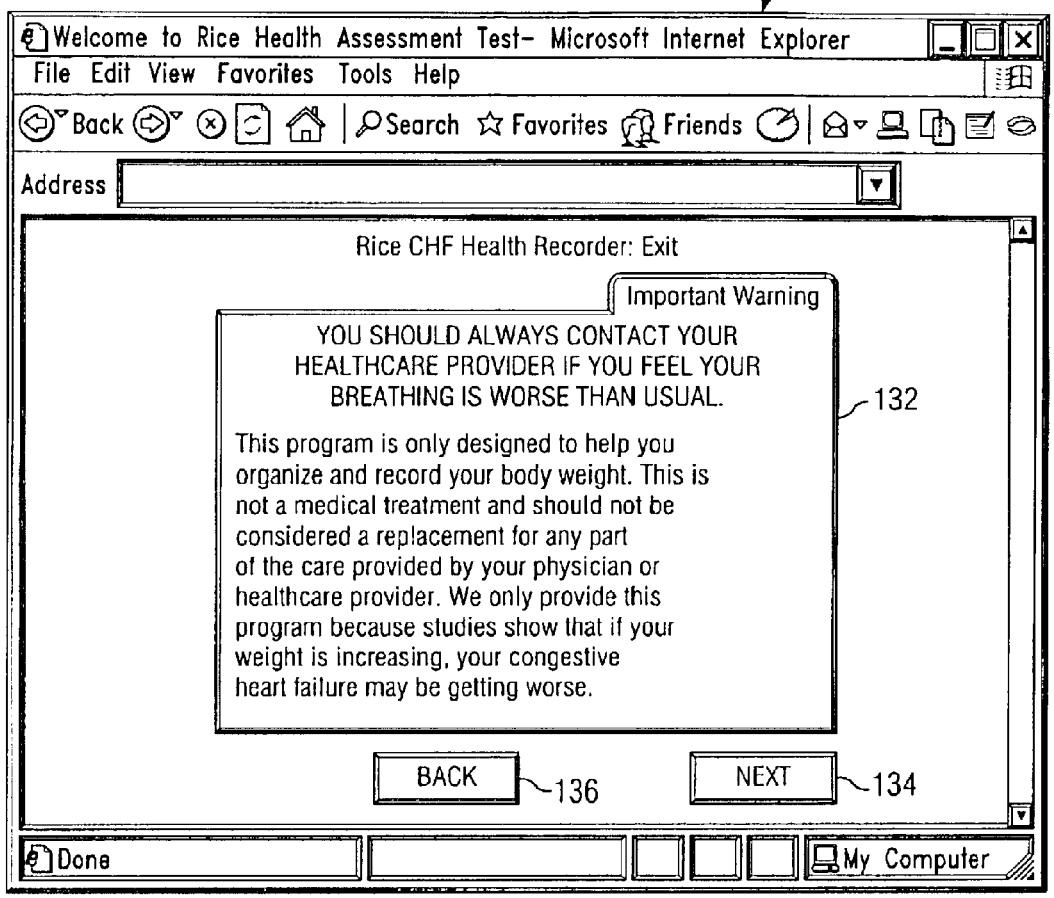
FIG. 12 shows an exemplary screen shot of an "EXIT" step according to an embodiment of the present invention.

In FIG. 12, exemplary screen shot 130 appears when the patient desires to exit the system. Screen shot 130 provides a disclaimer or warning to the patient in window 132 that the program does not replace medical care. The patient then exits the system by clicking "EXIT" icon 134, or may return to system operations by clicking "BACK" icon 136.

In another embodiment, the present invention takes information from a remotely located patient for statistical and medical analysis. The system then determines whether or not that information indicates a worsening medical condition that may require intervention by a healthcare professional. Instead of treating the medical condition from a remote location by using computers and the Internet with conventional schemes, the present invention informs the patient and/or healthcare team of the fact that there may be cause for additional review of the patient. This intervention is based upon the results of statistical or medical analysis of one or more pre-selected parameters associated with a diagnosed condition. As a result of this notification, the system encourages, or may actually schedule, the patient to visit a physician or other health care professional, rather than attempting to avoid office visits. As a result, the patient may receive more prompt and, perhaps, more effective, less intensive medical attention.

Figure 14:
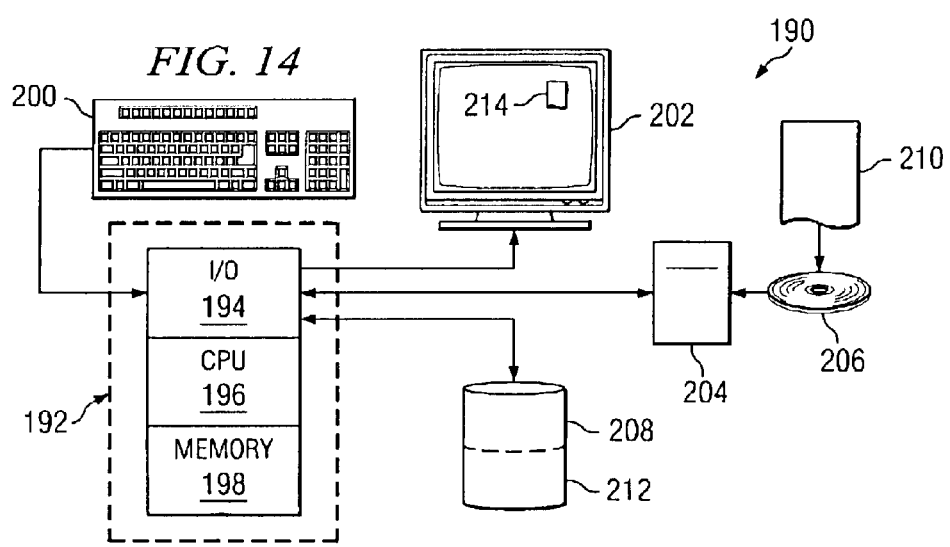
FIG. 14 illustrates a typical computer system for employing the many aspects of the present invention.

FIGS. 13 and 14 illustrate one embodiment of the statistical or medical analysis step 28 of FIG. 2 performed by the present invention. Through the analysis of a patient's condition, the present invention determines whether a violation has occurred of one or more rules that would give rise to an early-stage alert condition, as stated with reference to step 30 of FIG. 2.

In essence, the calculations of the present embodiment may be understood with reference to the spreadsheet of FIGS. 13A and 13B which shows two exemplary rules for which the present embodiment may test. Clearly, although the rules here stated relate to a CHF patient, similar or different rules could be established and tested consistent with the scope and purposes of the present invention.

A first rule, then, for which the spreadsheet of FIGS. 13A and 13B tests has to do with a patient's weight gain from one day to another. Rule 1 tests the deviation in daily weight against a minimum and a maximum weight gain. The minimum weight for which the system generates first alert is three pounds change in body weight. This amount may be based on such sources as the medical or scientific literature relating to the patient's condition. The maximum weight gain in this instance is five pounds, again, here based on the particular patient's condition and relevant scientific or medical literature. Rule 1 further calculates, using a value here called sigma. The value of sigma changes according to the patient's average weight over twenty consecutive measurements. From the sigma value a critical difference value of 2.88 times the square root of 2, which product is further multiplied by the relevant value of sigma value at the time of the patient weight measurement to yield a test value.

By initializing the below-described sigma at 0.98, an initial critical difference of 4.0 pounds over a one-day interval, for example, results. Thus, in the event of a weight change of 4.0 pounds, the present invention will transmit an alert to the patient.

A second rule for which this instance of the present embodiment tests in deviations in daily weight is also based on a moving or rolling twenty-weight measurement set. Such a set of measurements may be obtained, for example, through twenty days of continual daily weight measurements. Under this second rule, the present invention determines whether a minimum difference of two pounds is measured. No upper limit pertains to this second rule. The process derives a critical difference as a rolling average of twenty measurements, but here using a seven-measurement lag and three times the moving sigma, based on twenty prior measurements, as specified in detail below.

For purposes of the present embodiment and in the case of CHF, the seven-measurement lag may represent, for example, the set of twenty measurements where the most recent measurement occurred seven days ago and the least recent occurred twenty-seven days ago, with daily measurements occurring each of the intervening days.

In another embodiment, a different set of measurements might be more appropriate to take than the twenty measurements and seven-day lag used in the CHF case. Different diseases may develop acute exacerbations over varying amounts of time. It is important to exclude the timeframe of the evolving change from the baseline measurements. For example, in diabetic ketoacidosis, the time of evolving symptoms might be three days. So, in that example, it would be best to exclude the past three days measurements from the baseline data. This would have the effect of assuring the most effective early warning. In other words, data arising during the evolution of the exacerbation will not contribute to an artificially elevating baseline.

With more particular reference to spread sheet 140 of FIGS. 13A–B and to further explain the application of the two rules mentioned above, notice that there appears information, including the date of a patient's weight measurement of column 142 and the location of which the weight measurement occurred of column 144. For the exemplary patient "Bill Price," the weight measurements (e.g., 156 pounds taken at Dr. Minor's office on Nov. 29, 1999) appear on column 146. Column 148 shows the results of a rolling twenty-day average of patient Bill Price's weights (e.g., a weight of 165.375 calculated on Oct. 1, 2002). In Column 150 appears a further set of data which includes a rolling twenty-day average of patient Bill Price's weight, but measured with a twenty-day lag. That is, the data represents for the current day that information for which the most recent of the twenty days occurs twenty days prior.

A daily difference of measurements appears at column 152, followed by a scalar number, in column 154, representing the magnitude of the difference of the current day's measurement from the lagged twenty-day measurement from column 150. Column 156 calculates the average of up to the prior twenty-days measurements of the absolute value measurements appearing in column 154. The values for column 158 derive from the rules, and have the column title UCLmt, depicting a limit calculation based on the value of 3.27 times the MrBar value. Column 160 presents the number MR, as from column 154, but here revised according to comparison of if the MR value is greater than the UCLmt value, then the column 160 value is given as the MrBar value. Otherwise, the process uses the MR value for its further calculations. After twenty measurements, column 162 presents a further revised MrBar value, similar to that derived in column 156 and revised as the average of the past twenty values of Revised MR of column 160. These cumulative calculations derive the above-mentioned sigma value as the corresponding value of the Revised MR divided by 1.128, which column 164 contains. Then, based on the existing sigma value, the calculated value of the above-mentioned formula of 2.88 times the square root of 2 further multiplied by the sigma value of column 164 appears in column 166 as the critical value to be tested against. The rule one minimum appearing in column 168 is the greater of 3 or the critical difference value in column 166. Column 170 shows the determined value for weight according to the first rule limit. This value ranges from three to five pounds.

At column 172, a weight measurement moving average is taken for use in further calculations. Column 174 shows the results of a calculation for the moving average maximum variation from the moving average. In column 176 appears the critical difference calculation for the measurements against the rule two limits. The results of passing or failing the boundaries of rules one and two are shown in columns 178 and 180, respectively.

As should be clear from the above, the particular values for the rules and the number of rules may change depending on the particular chronic disease and the associated parameters for the disease for which early detection proves beneficial. Nonetheless, the clear import of the above description is that the present invention, through a potentially wide variety of embodiments provides a system and method of modeling chronic disease using a non-linear model together with a set of optimization routines to reduce healthcare costs and improve quality at the same time.

For many chronic conditions, the worsening of a patient's health does not follow a predictive model, and standardized therapies based upon broad demographic models are not suitable. These conditions make it difficult to treat some types of chronic diseases remotely.

In general, certain parameters are associated with certain types of chronic diseases. For example, a patient's weight is generally associated with congestive heart failure, whereas peak flow is generally associated with asthma. Glucose is generally associated with diabetes, whereas mood and depression charts are generally associated with mental health problems.

In an embodiment, statistical models that have been applied to chaotic systems, such as to weather forecasting by NOAA, are applied to one or more selected parameters of the patient associated with a chronic disease to determine the probability of worsening medical condition of the patient. By alerting the patient or their healthcare providers of the potentially worsening medical condition, the condition may be diagnosed, treated and managed early on by a healthcare professional, thereby avoiding more catastrophic and costly medical intervention later where the potential outcomes are not as favorable.

The methods and apparatus of the present invention, or certain aspects or portions thereof, take the form of program code (i.e., instructions) embodied in tangible media, such as floppy diskettes, CD-ROMS, hard drives, or any other machine-readable storage medium, wherein, when the program code is loaded into and executed by a machine, such as a computer, the machine becomes an apparatus for practicing the invention. The methods and apparatus of the present invention may also embody the form of program code transmitted over some transmission medium, such as over electrical wiring or cabling, through fiber optics, or via any other form of transmission, as known to those skilled in the art, wherein, when the program code is received and loaded into and executed by a machine such as a computer, the machine becomes an apparatus for practicing the invention. When implemented on a general-purpose processor, the program code combines with the processor to provide a unique apparatus that operates analogously to specific logic circuits.

FIG. 14 illustrates a typical computer system including traditional components of a personal computer. The present invention can have components similar to those shown, and furthermore, through accessing the Internet, the system may interact and interface with components on larger computers similar to examples illustrated in FIG. 14.

A general-purpose workstation computer 190 comprises a processor 192 having an input/output ("I/O") section 194, a central processing unit ("CPU") 196 and a memory section 198. The I/O section 194 is couples to keyboard 200, display unit 202, which shows visual output 214, disk storage unit 208, 212 and CD-ROM drive unit 204. The CD unit 204 can read CD-ROM medium 206 that typically contains programs 212 and data 208. The disk storage unit can be, or is connected to, a database or network server 210. The connection can be via a modem or other digital communication devices, such as wireless receiver and transmission components as used in PDAs and wireless communication devices known to one of ordinary skill in the art. The database server and network server 210 can be the same device or two separate but coupled devices.

Computer 190 may be a network appliance, personal computer, desktop computer, laptop computer, top box, web access device (such as WEBTVO (Microsoft Corporation)), or any like device. Use of computers also contemplates other devices similar to or incorporating computers, such as personal computers, television interfaces, kiosks, and the like.

Embodiments of the present invention may be implemented in a standalone system, entirely on the patient's computer hard drive so that there are no privacy or security concerns. The method according to embodiments of the present invention does not necessarily need a computer at all. A person may use a telephone, a personal digital assistant (PDA), or other means to record the data measurements described above. The patient also could be alerted by telephone, or such other means.

The present invention provides a computer-implemented method of impeding a progression of a disease condition or tracking the rehabilitation of a patient in order to reduce healthcare costs and improve patient quality of life. To accomplish this, a set of disease or condition-associated parameters is defined. These disease-associated parameters may be unique to a specific diagnosed disease such as, but not limited to: congestive heart failure, diabetes, asthma, emphysema, cancer, infarction, ischemia, arteriosclerosis, toxicity, mental disease, depression or arrhythmia. These parameters include but are not limited to: body weight, peak flow, glucose, number of nitroglycerin tablets taken, number of chest pain episodes, minutes walking without pain, ambulation distance without pain, number of emesis, number of episodes of diarrhea, mood charts, depression charts, and food/liquid intake.

Once a patient has been diagnosed with a specific disease condition, a series of repetitive measurements on a set of disease-associated parameters associated with the patient's diagnosed disease are collected on a frequent basis. The data may either be automatically entered or manually entered into the computer system shown in FIGS. 13A–B. For example, as previously discussed, the patient may enter their body weight through a patient interface presented on the computers display, via keyboard 200, or through a data collection device, such as a scale, directly coupled to I/O interface 194. This illustrates an objective measurement. However, some measurements, such as those associated with mental disease, may rely on subjective measurements taken by the patient or health care provider.

Figure 1B:
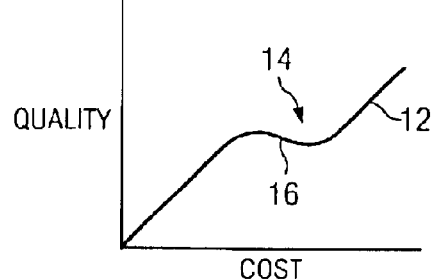

This data may first be evaluated to eliminate data entry errors or health problems indicated by that single data point. Next, the computer, either locally or remotely, may perform a series of analyses to identify potential future problems that may require medical intervention. By early identification of these potential problems, the patient or their healthcare provider may apply secondary prevention techniques to address or reduce the risk of these potential future problems. The failure to identify and take secondary prevention actions in many cases accounts for the "quality valley" 14 shown in FIG. 1B that is associated with increased medical costs and reduced outcomes. Early identification, and proactive measures helps to reduce medical costs and increase the likely of favorable outcomes, or impede the progression of a disease. The failure to address these potential problems will often result in later more invasive medical intervention with less favorable outcomes. This condition often accounts for "quality valley" 14.

The statistical or medical analysis performed on the data may compare the data to predetermined control limits, trend analysis, tests for special cases, such as the Western Electric Rules, or other such analyses as are known to those skilled in the art.

The present invention may be implemented by a computer program executed within a computer, such as a personal computer, personal data assistant, network appliance, web access device, computer kiosks, television interfaces or like device. The program may comprise instructions that enable to processor to perform the tasks of: (1) collecting and evaluating the repetitive measurements supplied by the patient or healthcare provider; (2) performing statistical analysis on a series or history of repetitive measurements; and (3) alerting the patient or health care provider to those analyses which indicate a potential future problem. These steps allow the patient and/or healthcare team to apply secondary prevention techniques that address the potential future problem. Thus, allowing the patient to enjoy a more favorable outcome and reduced health care expense.

In one embodiment, a computer performs the process of collecting clinical parameters, processing, data alerts, and subsequent data. Another embodiment uses an automated telephone system coupled to a computer system. In such a system, a patient "signs up" for the service and receives a password. As part of the sign-up process, the patient's disease, home phone number and preferred call times are submitted. The automated system then calls the patient on a predetermined schedule. A computer-generated voice asks for the patient's password, and then prompts entry of the patient's data. For example, in the case of congestive heart failure, the collected data is body weight. The automated system verifies the integrity of the data and ends the phone call. An "alert" advises the patient of an abnormal reading, and may transfer the patient directly and automatically to a physician's office, answering service, or other requested number. The automated system may also automatically re-call the patient to confirm understanding of the alert.

Such a system may use voice recognition and synthesis in all or part as the patient interfaces. Similarly, other information transactions can be accomplished on various wireless and PDA-type devices.

From the above description of the invention it is manifest that various equivalents can be used to implement the concepts of the present invention without departing from its scope. Moreover, while the invention has been described with specific reference to certain embodiments, a person of ordinary skill in the art would recognize that changes could be made in form detail without departing from the spirit and the scope of the invention. The described embodiments are to be considered in all respects as illustrative and restrictive. It should also be understood that the invention is not limited to the particular embodiments described herein, but is capable of many equivalents rearrangements modifications, and substitutions without departing from the scope of the invention.

What is claimed is:

1. A computer implemented method of impeding a progression of a disease within a patient comprising the steps of:
    defining a set of disease associated parameters;
    performing repetitive measurements on said set of disease associated parameters;
    evaluating said repetitive measurements of disease associated parameters;
    performing statistical analysis on a history of said repetitive measurements of disease associated parameters, wherein said statistical analysis comprises a Deming Statistical Method;
    alerting the patient to those statistical analyses which indicate a potential future problem that requires intervention; and
    applying secondary prevention techniques to address said potential future problem.

2. The method of claim 1, wherein said step of performing repetitive measurements further comprises entering said repetitive measurements on said set of disease associated parameters through a patient interface to the computer.

3. The method of claim 1, wherein said statistical analysis performing step uses a history of said repetitive measurements occurring at a defined period of time preceding the most recent of said performed repetitive measurements.

4. The method of claim 1, further comprising the step of storing in a computer memory said history of said repetitive measurements of disease-associated parameters.

5. The method of claim 1, wherein said steps of evaluating said repetitive measurements, performing statistical analysis on said history of said repetitive measurements, and alerting the patient to statistical analyses which indicate a potential future problem are performed by executing a set of instructions encoded within a computer memory.

6. The method of claim 1, wherein the disease is selected from the group consisting of congestive heart failure, diabetes, asthma, emphysema, cancer, infarction, ischemia, arteriosclerosis, toxicity, mental disease, depression and arrhythmia.

7. The method of claim 6, wherein said set of disease associated chaotic parameters comprise at least one parameter selected from the group consisting of body weight, peak flow, glucose, number of nitroglycerin tablets taken, number of chest pain episodes, minutes walking without pain, ambulation distance without pain, number of emesis, number of episodes of diarrhea, mood charts, depression charts, and food/liquid intake.

8. The method of claim 1, wherein the computer is coupled to a network and communicates with the patient's health care team.

9. The method of claim 1, wherein the computer uses an audio interface to interact with the patient.

10. The method of claim 9, wherein the audio interface uses voice synthesis and recognition over a telephone to automatically gather data from the patient.

11. The method of claim 10, wherein the audio interface connects the patient automatically to a health care provider when said statistical analysis indicate a potential future problem that requires intervention.

12. The method of claim 1, wherein the computer couples to a wireless or PDA device.

13. The method of claim 1, wherein said computer comprises;
    a computer processor;
    a computer memory operable to store lines of code coupled to said computer processor wherein said lines of code load into said computer processor and execute said steps of evaluating said repetitive measurements, performing statistical analysis on said history of said repetitive measurements, and alerting the patient to those statistical analyses which indicate a potential future problem.

14. An apparatus to identify potential future problems in a patient that will require medical intervention, comprising:
    a computer device, wherein said computer device further comprises computer memory and a computer processor, wherein said computer memory is operable to store lines of code that when executed by said computer processor execute the steps of:
    collecting repetitive measurements on a set of disease associated chaotic parameters and storing said repetitive measurements in a data storage location;
    evaluating said repetitive measurements of disease associated chaotic parameters;
    combining said repetitive measurements of disease associated chaotic parameters with historical repetitive measurements stored in said data storage location;
    performing statistical analysis on a history of said repetitive measurements of disease associated chaotic parameters, wherein said statistical analysis comprises a Deming Statistical Method; and
    alerting the patient to a potential future problem that requires intervention;
    a healthcare team that applies secondary prevention techniques to address said potential future problem.

15. The apparatus of claim 14, wherein said repetitive measurements are entered through a patient interface to the computer.

16. The apparatus of claim 14, wherein said computer processor is further capable or executing the step of storing in memory said history of said repetitive measurements of disease associated chaotic parameters.

17. The apparatus of claim 14 wherein the disease is selected from the group consisting of congestive heart failure, diabetes, asthma, emphysema, cancer, infarction, ischemia, arteriosclerosis, toxicity, mental disease, depression and arrhythmia.

18. The apparatus of claim 17, wherein said set of disease associated chaotic parameters comprise at least one parameter selected from the group consisting of body weight, peak flow, glucose, number of nitroglycerin tablets taken, number of chest pain episodes, minutes walking without pain, ambulation distance without pain, number of emesis, number of episodes of diarrhea, mood charts, depression charts, and food/liquid intake.

19. The apparatus of claim 14, wherein the computer is coupled to a network and communicates with healthcare team, and wherein said healthcare team contacts the patient.

20. The apparatus of claim 14, wherein the computer is a standalone device.

21. The apparatus of claim 14, wherein said computer comprises a personal computer, personal data assistant, network appliance, web access device, computer kiosks, or television interfaces.

22. A computer implemented method of impeding a progression of a disease within a patient comprising the steps of:
    defining a set of disease associated chaotic parameters;
    collecting repetitive measurements on said set of disease associated chaotic parameters through a patient interface to the computer;
    evaluating said repetitive measurements of disease associated chaotic parameters;

storing in a computer memory a history of said repetitive measurements of disease associated chaotic parameters;

performing statistical analysis on said history of said repetitive measurements of disease associated chaotic parameters, wherein said statistical analysis comprises a Deming Statistical Method;

alerting the patient or a healthcare team to those statistical analyses which indicate a potential future problem that requires intervention, and wherein the healthcare team is coupled to a network that communicates with the computer; and applying secondary prevention techniques to address said potential future problem.

23. The method of claim 22, wherein the disease is selected from the group consisting of congestive heart failure, diabetes, asthma, emphysema, cancer, infarction, ischemia, arteriosclerosis, toxicity, mental disease, depression and arrhythmia, and wherein said set of disease associated chaotic parameters comprise at least one parameter selected from the group consisting of body weight, peak flow, glucose, number of nitroglycerin tablets taken, number of chest pain episodes, minutes walking without pain, ambulation distance without pain, number of emesis, number of episodes of diarrhea, mood charts, depression charts, and food/liquid intake.

24. The method of claim 22, wherein said computer comprises;

a computer processor;

a computer memory operable to store lines of code coupled to said computer processor wherein said lines of code load into said computer processor and execute said steps of evaluating said repetitive measurements, performing statistical analysis on said history of said repetitive measurements, and alerting the patient to those statistical analyses which indicate a potential future problem.

25. A computer implemented method of reducing healthcare costs, comprising the steps of:

diagnosing a patient with a disease condition;

defining a set of disease associated parameters;

performing repetitive measurements on said set of disease associated parameters;

evaluating said repetitive measurements of disease-associated parameters;

performing statistical and medical analysis on a history of said repetitive measurements of disease associated parameters;

alerting the patient to those statistical or clinical analyses which indicate a potential future problem that requires intervention, wherein said statistical analysis comprises a Deming Statistical Method; and applying secondary prevention techniques to address said potential future problem and/or impede a progression of said disease condition.

26. The method of claim 25, wherein said step of performing repetitive measurements further comprises entering said repetitive measurements on said set of disease associated parameters through a patient interface to the computer.

27. The method of claim 25, further comprising the step of storing in a computer memory said history of said repetitive measurements of disease-associated parameters.

28. The method of claim 25, wherein said steps of evaluating said repetitive measurements, performing statistical analysis on said history of said repetitive measurements, and alerting the patient to statistical analyses which indicate a potential future problem are performed by executing a set of instructions encoded within a computer memory.

29. The method of claim 25, wherein the disease is selected from the group consisting of congestive heart failure, diabetes, asthma, emphysema, cancer, infarction, ischemia, arteriosclerosis, toxicity, mental disease, depression and arrhythmia.

30. The method of claim 29, wherein said set of disease associated parameters comprise at least one parameter selected from the group consisting of body weight, peak flow, glucose, number of nitroglycerin tablets taken, number of chest pain episodes, minutes walking without pain, ambulation distance without pain, number of emesis, number of episodes of diarrhea, mood charts, depression charts, and food/liquid intake.

31. The method of claim 25, wherein the computer is coupled to a network and communicates with the patient's health care team.

32. The method of claim 25, wherein the computer is a standalone device.

* * * * *